United States Patent [19]
Leonard

[11] 4,255,144
[45] Mar. 10, 1981

[54] DEVICE FOR FIXING A DENTAL INSTRUMENT IN A HANDPIECE

[75] Inventor: Henri Leonard, Besancon, France

[73] Assignee: Micro-Mega S.A., France

[21] Appl. No.: 34,678

[22] Filed: Apr. 30, 1979

[30] Foreign Application Priority Data

Jun. 1, 1978 [FR] France .................................. 78 16972

[51] Int. Cl.³ ................................................ A61C 1/14
[52] U.S. Cl. .................................... 433/127; 279/41 R
[58] Field of Search ............................ 279/102, 20, 41; 433/127, 129

[56] References Cited

U.S. PATENT DOCUMENTS

| 2,785,464 | 3/1957 | Hoffmeister | 433/133 |
| 3,098,299 | 7/1963 | Page | 433/127 |
| 3,107,101 | 10/1963 | Garnier et al. | 433/127 |

Primary Examiner—Robert Peshock
Attorney, Agent, or Firm—Robert E. Burns; Emmanuel J. Lobato; Bruce L. Adams

[57] ABSTRACT

This fixing device comprises a clamping claw consisting of a pair of diametrally opposed semi-cylindrical curved shells each connected by means of a small bar parallel to the shell generatrices to an end pivot pin, the bars extending on either side of the shells. An axial bore is formed through the claw and the pair of pivot pins are provided, in the vicinity of their junction with the corresponding bars, with a circular land having a diameter at least substantially equal to that of the shells, a cylindrical sleeve of flexible and sterilization-resistant material being slipped over these lands and extending therebetween in order to impart the necessary fluid-tightness to the axial bore in relation to the interior of the handpiece.

4 Claims, 4 Drawing Figures

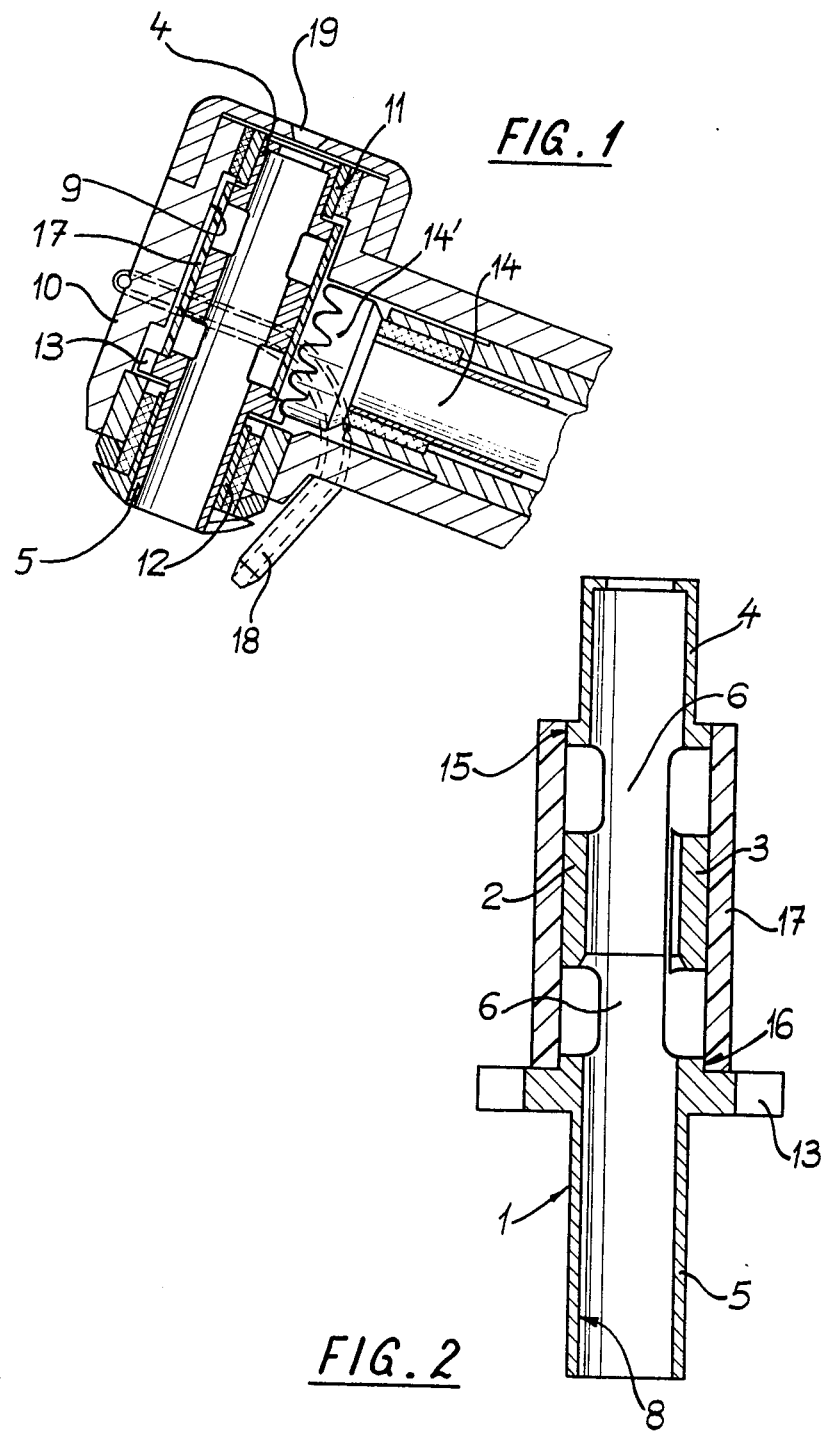

DEVICE FOR FIXING A DENTAL INSTRUMENT IN A HANDPIECE

FIELD OF THE INVENTION

This invention relates to a device for fixing a rotary dental instrument such as a bur in a handpiece.

DESCRIPTION OF THE PRIOR ART

In U.S. Pat. No. 3,107,101 the applicant discloses a fixing device in which the bur is introduced into a clamping claw provided with an axial hole in which the bur can be tightened; this claw consists of two semi-cylindrical, curved and diametrally opposed clamping portions or shells separated by an axial slot and each rigid with a small bar parallel to the generatrices of the shells, said bar extending on either side of said shells, in order to impart thereto an elasticity sufficient to properly clamp the bur, an axial pivot portion being secured to the bars at either ends of the assembly, one pivot portion carrying a claw driving pinion, and the two pivot portions are journaled in corresponding bearings provided at the two ends of said head.

A device of this character is intended more particularly for mounting in the head of a contra-angle. For this purpose, the contra-angle head is provided with an axial passage in which the two bearings adapted to receive the pair of pivot portions of the holding member are force fitted. The bur is easily fixed in position by introducing it axially into the holding member so that it can be properly clamped between the two shells. However, its removal is more delicate and in general to avoid any risk of damaging the various component elements an aperture is provided in the upper portion of the head so that the operator can introduce a rod into this aperture for pushing the bur out of the contra-angle.

When working in the patient's mouth, the spray water might penetrate through this hole into the claw and seep in between the claw and the bur and finally penetrate into the contra-angle. This spray water might also penetrate into the front portion of the head, between the bur and the claw.

Now this penetration of spray water into the contra-angle head is particularly detrimental when using a micromotor coupled directly to the handpiece, for in this case water might rise up into the mirror and deteriorate it.

SUMMARY OF THE INVENTION

It is the essential object of this invention to avoid this inconvenience.

For this purpose, the device according to this invention is characterized in that the two pivot portions are each provided, in the vicinity of their junction with the small bars, with a land or circular bearing surface having a diameter at least approximately equal to the outer diameter of said semi-cylindrical shells, that a cylindrical sleeve of flexible material capable of withstanding sterilization is slipped onto said lands or bearing surfaces and extends therebetween, so as to render said axial hole fluid-tight with respect to the interior of the handpiece, and that the diameter of said lands or bearing surfaces and the thickness of said sleeve are such that the outer periphery of the sleeve does not contact the other component elements of the head.

According to a preferred form of embodiment, the sleeve consists of polytetrafluoroethylene(Teflon).

Thus, a perfect seal is obtained, and any water seeping into the claw cannot penetrate into the contra-angle.

BRIEF DESCRIPTION OF THE DRAWING

FIG. 1 illustrates in axial section a contra-angle head incorporating the device of this invention;

FIG. 2 is an axial section showing on a larger scale the clamping claw with its sleeve;

DESCRIPTION OF THE PREFERRED EMBODIMENTS

Figure 3:
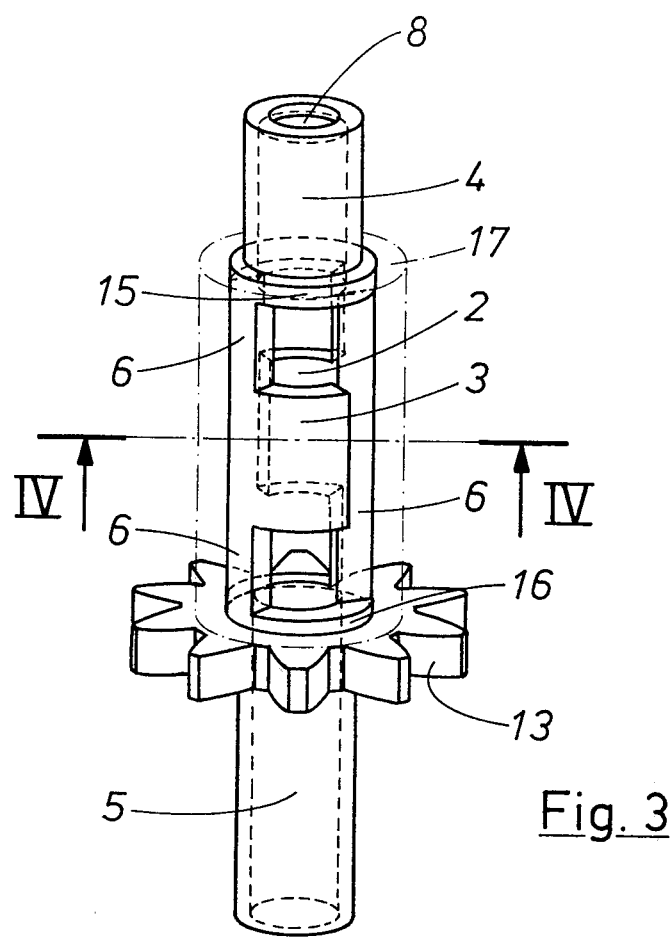
FIG. 3 is a perspective view of the clamping claw with the sleeve shown in dot and dash lines.
Figure 4:
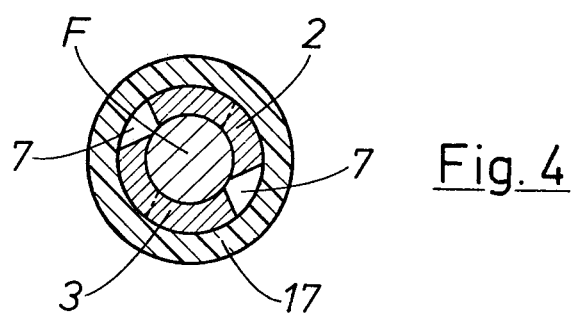
FIG. 4 is a cross-sectional view of the claw, the section being taken along the line IV—IV of FIG. 3 and showing the bur and sleeve.

The clamping claw 1 consists of a pair of diametrally opposed clamping portions or shells 2, 3 of semi-cylindrical configuration, separated by a pair of axial slots 7 and each connected through small bars 6 to a pair of end pivot portions 4, 5, said bars 6 being parallel to the generatrices of shells 2, 3 and extending on either side thereof so as to act as torsion bars. An axial bore 8 extending through the claw 1 from end to end is adapted to receive the shank F (FIG. 4) of a bur (not shown) so as to resiliently clamp the latter between the shells 2, 3 which, for this purpose, are slightly curved inwardly towards the centre.

This claw 1 is adapted to be mounted in an axial bore 9 of the contra-angle head 10, the end pivot portions 4, 5 revolving in corresponding bearings 11, 12, respectively, fitted in the bore 9. Besides, the lower pivot portion 5 of claw 1 is provided in a manner known per se with an integral pinion 13 adapted to be rotatably driven from the motor (not shown) through the motor output arbor 14 and the end pinion 14' thereof. On the other hand, the contra-angle head comprises in the known fashion an external pipe 18 for supplying cooling fluid to the instrument and also an orifice 19 formed in its upper portion opposite the bur for introducing a bur extraction rod (not shown) when it is desired to replace or simply remove the bur.

The pivot portions 4, 5 of claw 1, are provided, in the vicinity of their junctions with the small bars 6, with circular lands or bearing surfaces 15, 16 having a diameter substantially equal to the outer diameter of the semi-cylindrical shells 2 and 3. Force fitted on these circular lands or surfaces 15, 16 is a tube or cylindrical sleeve 17 of flexible material capable of withstanding sterilization, this sleeve enclosing the claw 1 between said lands 15 and 16. According to a preferred form of embodiment of the instant invention, the material constituting this tube or sleeve 17 is polytetrafluoroethylene (Teflon) so that a highly reliable seal is obtained. The diameter of these lands 15 and 16 and the thickness of the sleeve 17 are so calculated that the outer periphery of the sleeve does not contact the other component elements of the head.

From the foregoing it is clearly apparent that the presence of the sleeve 17 will render perfectly fluid-tight the communication between the axial bore 8 of claw 1, and the interior of the contra-angle. Thus, should any water pass through the orifice 19 provided at the top of the contra-angle head or seep into the lower portion of this head between the bur (not shown) and the claw 1, it could not penetrate into the contra-angle. Of course, this fixing device may be used for fixing any desired dental instrument, such as burs, reamers, Hedstroem files, broaches, spiral fillers, etc.

What is claimed is:

1. In the head of a dental handpiece, the combination of dental instrument clamping means comprising axially spaced coaxial tubular pivot portions, a pair of semi-cylindrical and diametrically opposed clamping portions disposed between said pivot portions, said clamping portions being separated from one another by axial slots and each being connected by torsion by portions with said pivot portions, bearing means in said head rotatably supporting said pivot portions, a pinion fixed on one of said pivot portions for driving said instrument clamping means in rotation, each of said pivot portions having adjacent its junction with said torsion bar portions a circular land having a diameter at least approximately equal to the outer diameter of said semi-cylindrical clamping portions and a cylindrical sleeve of flexible and sterilization-resistant material enclosing said clamping portions and having opposite ends force-fitted on said lands of said pivot portions to provide a fluid-tight seal between the interior and exterior of said instrument clamping means.

2. A combination according to claim 1, in which the diameter of said lands and the thickness of said sleeve are such that the outer periphery of said sleeve is free of other components of said head.

3. A combination according to claim 1, in which said pinion is positioned adjacent said circular land of the respective pivot portion, and an end of said sleeve abuts said pinion.

4. A combination according to claim 1, in which said sleeve is of polytetrafluoroethylene.

* * * * *